United States Patent [19]

Sherman

[11] Patent Number: 5,798,333

[45] Date of Patent: Aug. 25, 1998

[54] WATER-SOLUBLE CONCENTRATES CONTAINING CYCLOSPORINS

[76] Inventor: Bernard C. Sherman, 50 Oldcolony Rd., Willowdale, Ontario, Canada, M2L 2K1

[21] Appl. No.: 715,033

[22] Filed: Sep. 17, 1996

[51] Int. Cl.⁶ .................................................. A61K 38/00
[52] U.S. Cl. ........................................................ 514/11
[58] Field of Search ............................................ 514/11

[56] References Cited

U.S. PATENT DOCUMENTS

| | | | |
|---|---|---|---|
| 4,388,307 | 6/1983 | Sandoz | 514/11 |
| 5,342,625 | 8/1994 | Sandoz | 514/11 |
| 5,583,105 | 12/1996 | Kovacs | 514/11 |

FOREIGN PATENT DOCUMENTS

| | | |
|---|---|---|
| 272653 | 12/1996 | New Zealand . |
| 2230440 | 10/1990 | United Kingdom . |
| 00222 | 10/1994 | WIPO . |
| 95/11039 | 4/1995 | WIPO . |

*Primary Examiner*—Robert Gerstl
*Attorney, Agent, or Firm*—Nixon & Vanderhye P.C.

[57] ABSTRACT

The invention is directed to pharmaceutical compositions which enable high concentrations of a cyclosporin and are water-soluble, such that the compositions will dissolve in aqueous media without precipitation of the cyclosporin. The compositions comprise a cyclosporin dissolved in tocophersolan and a hydrophillic organic solvent, preferably propylene glycol.

15 Claims, No Drawings

WATER-SOLUBLE CONCENTRATES CONTAINING CYCLOSPORINS

TECHNICAL FIELD

The invention is directed to pharmaceutical compositions which facilitate the administration of cyclosporins, particularly for oral ingestion.

BACKGROUND ART

Cyclosporins are hydrophobic and have low solubility in aqueous media. This makes it difficult to design compositions which exhibit satisfactory absorption into systemic circulation after oral administration.

Cyclosporins can be dissolved in an organic solvent (e.g. ethanol or propylene glycol), but if the solvent is water-soluble, when the composition is mixed with gastrointestinal fluid, the cyclosporin will precipitate into particles which are not absorbed.

Various methods of overcoming this problem are known in the prior art.

U.S. Pat. No. 4,388,307 discloses compositions comprising a cyclosporin in an emulsion preconcentrate that is not water-soluble, but forms an emulsion upon being mixed into gastrointestinal fluids. The commercial product sold under the tradename Sandimmune is made according to U.S. Pat. No. 4,388,307, and, more specifically, comprises cyclosporine dissolved in a solvent system comprising ethanol, a vegetable oil and a surfactant. Although this composition was superior to previously known compositions, it still exhibits absorption that is less than the maximum possible and is variable. Also, the use of ethanol is undesirable, as ethanol is volatile; hence capsules of Sandimmune which contain this emulsion preconcentrate must be individually packaged in metallic pouches to avoid loss of ethanol by evaporation.

U.S. Pat. No. 5,342,625 discloses emulsion preconcentrates that are similar to ones disclosed in U.S. Pat. No. 43,883,007, in that they contain, in addition to the cyclosporin, a hydrophillic phase, a lipophilic phase and a surfactant.

It is stated that compositions according to U.S. Pat. No. 5,342,625, when added to water, disperse into droplets of smaller size than prior art compositions, thus leading to improved absorption, and these emulsion preconcentrates are referred to as microemulsion preconcentrates.

International Patent Application Number PCT/CA94/00222 discloses improved emulsion preconcentrates in which the principal solvent for the cyclosporin is an alcohol having low solubility in water. Such alcohols are referred to as hydrophobic alcohols. It is disclosed that a hydrophobic alcohol can be used in place of the combination of hydrophillic and hydrophobic solvents.

Another approach to overcoming the hydrophobicity of cyclosporins is to incorporate in the composition, along with the cyclosporin, a water-soluble surfactant which will solubilize the cyclosporin by forming micelles when the composition is mixed with water. Such compositions will be referred to herein as "solution preconcentrates".

This approach has the advantage of eliminating the need for a hydrophobic organic solvent which is required in all formulations of emulsion preconcentrates or microemulsion preconcentrates.

An example of a solution preconcentrate is the product sold under the tradename Sandimmune for intravenous use.

In this composition, 1 mL contains 50 mg cyclosporine, and 650 mg polyoxyethylated castor oil, dissolved in ethanol. This composition is intended to be diluted in water (i.e. 0.9% sodium chloride injection or 5% dextrose injection) before use.

The polyoxyethylated castor oil is a water-soluble surfactant which solubilizes the cyclosporine in water by forming micelles, and the purpose of the ethanol is to solubilize the cyclosporine in the composition to prevent precipitation before the composition is dispersed in the water.

The quantity of 650 mg polyoxyethylated castor oil is the minimum amount needed to fully solubilize 50 mg cyclosporine in water.

While this composition is suitable for injectable use, it is not practical as a dosage form for routine oral administration, for the following reasons:

1. The concentration of cyclosporine in the composition is too low. It is desirable to administer cyclosporine in dosage units of up to 100 mg. As the maximum fill for a capsule of a size that can be easily swallowed is about 1 mL, the concentration of cyclosporin must be about 100 mg per mL (or 100 mg per gram) or more to enable a capsule of 100 mg strength.
2. The amount of surfactant (650 mg per 50 mg cyclosporine) is excessive and gives rise to concern about toxicity of the surfactant in chronic use.
3. Ethanol is a volatile solvent, and any dosage form containing ethanol must be protected against evaporation of the ethanol.

The prior art also discloses other improved solution preconcentrates which achieve higher concentration of the cyclosporin and lower quantities of surfactants.

For example U.K. Patent Application number GB2230440A discloses compositions comprising a cyclosporin, a fatty acid saccharide monoester as the surfactant, and a diluent or carrier. The diluent or carrier is typically ethanol, an alkylene glycol or polyol, a polyalkylene glycol, an alkylene polyol ether or ester paraffin, or an organosilicon oxide polymer.

However, the solution preconcentrate compositions disclosed in this publication are less than ideal in several respects.

In particular:

i) In compositions which take the form of a solution of the cyclosporin and surfactant in an organic solvent, the amount of organic solvent required is more than desirable, giving rise to toxicity concerns.

ii) Where reduced amounts of organic solvent are used, the formulations may exhibit precipitation of some of the cyclosporin on prolonged storage.

iii) Some of the compositions are prepared by dissolving the cyclosporin and surfactant in ethanol or another volatile organic solvent, and the quantity of organic solvent is then reduced by evaporation. This requires the additional step of evaporation. Moreover, upon evaporation of the solvent, the composition may have insufficient solvent to prevent precipitation of some of the cyclosporine on prolonged storage.

It is thus the object of the present invention to enable a solution preconcentrate containing a cyclosporin which has most or all of following characteristics.

1. It consists of a solution of the cyclosporin in a combination of at least one water-soluble surfactant and at least one hydrophillic organic solvent.
2. The concentration of cyclosporin within the composition is enabled to be as high as or higher than about 100 mg per mL or 100 mg per gram, as needed to enables capsule containing 100 mg of the cyclosporin.

3. Upon addition to water (or to gastrointestinal fluid or other aqueous medium), the composition will dissolve to form a clear or almost clear solution, without precipitation of the cyclosporin.
4. The composition is stable against precipitation of the cyclosporin on prolonged storage.
5. The surfactant contained within the composition is relatively nontoxic.
6. The organic solvent contained within the composition is relatively nontoxic and the amount required is relatively small so as not to give rise to concerns of toxicity.
7. Preparation of the composition does not require evaporation of any organic solvent.
8. The organic solvent used in the composition is relatively non-volatile, so that the composition can be contained within gelatin capsules without the need for the capsules to be packaged in a protective container to prevent evaporation of the solvent.

SUMMARY OF THE INVENTION

The term "cyclosporins" as used herein shall mean the class of nonpolar polypeptides, defined in the Merck Index, Eleventh Edition. One such cyclosporin is cyclosporin A, also known as "cyclosporine" and hereinafter referred to as "cyclosporine", known to be therapeutically active as an immunosuppressant.

The term "composition" as used herein will be understood as meaning any pharmaceutical dosage form containing a cyclosporin along with inactive ingredients that are pharmaceutically acceptable. The term "pharmaceutically acceptable" will be understood to mean having sufficiently low toxicity to be useable in a composition in the amount required.

In order to accomplish the objects of the invention it is necessary to have a combination of surfactant and hydrophillic organic solvent that enables use of relatively small quantities of both. For this to be possible it is necessary to use a surfactant that has the following characteristics, in addition to being nontoxic:

I) it must be an efficient solubilizer of the cyclosporin in water; that is to say the amount required to solubilize a given amount of cyclosporin in water must be relatively small.

ii) the surfactant must itself be a solvent for the cyclosporin; that is to say, the cyclosporin must to some extent be soluble in the surfactant even in the absence of water or another solvent, in order to minimize the amount of organic solvent that must be added to render the cyclosporin fully dissolved within the composition.

It has been found that a suitable surfactant meeting these requirements is d-alfa tocopheryl polyethylene glycol 1000 succinate, which is sold by Eastman Chemical Products Inc. under the name Vitamin E TPGS. This compound is also known as tocophersolan, and will be referred to hereinafter as tocophersolan.

Accordingly, compositions within the scope of the present invention will comprise a cyclosporin and tocophersolan co-dissolved in a relatively small amount of a hydrophillic nontoxic organic solvent. For purposes of this specification, the term hydrophillic will mean having a solubility of at least 0.1 g per 100 g of water at 20° C.

DETAILED DESCRIPTION OF THE INVENTION

As aforesaid, compositions within the scope of the invention are solution preconcentrates containing a cyclosporin, such that when the composition is dispersed in an aqueous medium the composition will dissolve without precipitation of the cyclosporin. The compositions of the invention comprise a cyclosporin and tocophersolan dissolved in a hydrophillic nontoxic organic solvent.

Tocophersolan is a water-soluble nontoxic surfactant having a melting point of about 36° C. It has been found that the amount of tocophersolan required to dissolve cyclosporine in water is about 7.5 parts tocophersolan per part cyclosporine by weight.

Accordingly, if tocophersolan is to be the sole surfactant in the solution preconcentrate composition, it should be present at a level of about 7.5 parts tocophersolan per part cyclosporine.

Experiments were performed in which tocophersolan was liquified by heating it to above 36° C. and, various amounts of cyclosporine were added. The amount of cyclosporine that is soluble in tocophersolan was found to be substantially less than 1 part per 7.5 parts tocophersolan by weight.

Hence, in order to form a composition that is a solution preconcentrate and which comprises cyclosporine and about 7.5 parts tocophersolan per part cyclosporine, and in order to have the cyclosporine fully dissolved within the composition, it is necessary to add some quantity of a pharmaceutically acceptable hydrophillic organic solvent.

The solvent selected should be an efficient solvent for cyclosporine, and also a solvent for tocophersolan.

Preferred organic solvents meeting these criteria include but are not necessarily limited to propylene glycol and various monoalcohols, including ethanol, benzyl alcohol, hexanol, and phenethyl alcohol.

Most preferred is propylene glycol because it has low toxicity and low volatility in addition to being an efficient solvent for cyclosporine.

The amount of propylene glycol needed to provide a stable solution of cyclosporine and tocophersolan is about 1 g per g of cyclosporine. A suitable solution preconcentrate will thus consist of 1 part cyclosporine, 7.5 parts tocophersolan and 1 part propylene glycol.

This composition can be made by mixing the ingredients at a temperature of above 36° C. until a clear solution is formed. On cooling to 20° C. the solution will solidify. When it is added to water either in solid form, or in liquid form after rewarming, it gradually dissolves to form a clear or virtually clear solution.

It can thus be seen that the invention enables solution preconcentrates wherein the concentration of the cyclosporine substantially exceeds 1 part per 15 parts by weight, and more particularly, the invention enables concentrations as high as 100 mg per mL or 100 mg per gram, or even higher.

It will be understood that another pharmaceutically acceptable hydrophillic solvent may be used in place of propylene glycol provided that it has adequate solvent capacity for both the cyclosporine and tocophersolan, or that a combination of solvents may be used.

It will also be understood that compositions within the scope of the invention may comprise other ingredients in addition to the cyclosporine, tocophersolan and a hydrophillic organic solvent, such other ingredient being added as co-surfactants, co-solvents, thickeners, or for other purposes.

For example, an additional surfactant may be used as a co-surfactant to reduce the quantity of tocophersolan needed and thereby increase the concentration of the cyclosporine within the composition. Sodium dodecyl sulfate is preferred as a co-surfactant. For each 1 part of sodium dodecyl sulfate that is added, the amount of tocophersolan required to make the composition fully water soluble is reduced by about 5 parts. Use of a large amount of sodium dodecyl sulfate is not desirable because it is substantially more toxic than tocophersolan.

As another example, an ingredient may be added to raise the melting point of the composition. A composition comprised solely of cyclosporine, tocophersolan and propylene glycol will have a melting point of under 35° C. and perhaps under 30° C. If the composition is to be used, for example, as a fill for a two piece hard gelatin capsule, it is desirable to have a melting point above 35° C. so that the contents of the capsule will remain solid or semi-solid at any temperature that the capsule is likely to endure in storage or shipment. This will avoid the need to seal the capsules, which would otherwise be needed to prevent leakage of liquid contents out of the capsule.

A suitable ingredient to be added to raise the melting point is a polyethylene glycol having an average molecular weight of 1000 or above. Such polyethylene glycols are sold under the tradename Carbowax by Union Carbide Corporation.

Particularly suitable are Carbowax 3350 which has an average molecular weight of 3350 and a melting range of 54° to 58° C. or Carbowax 8000 which has an average molecular weight of 8000 and a melting range of 60° to 63° C.

Blending of only a few percent by weight of Carbowax 8000 to the composition will raise the melting range of the composition such that it will remain a solid or a non-flowing semi-solid at temperatures as high as 40° C. or even higher. The blending into the composition will preferably be done at a temperature above the melting range of the Carbowax 8000.

Particularly if the composition is a liquid at room temperature, it may be used directly as an end dosage form for oral administration as a solution preconcentrate. That is to say, it may be directly ingested as a solution preconcentrate in liquid form, which will, after ingestion, dissolve in the gastrointestinal fluids.

Alternatively, prior to oral ingestion, the composition may be diluted by mixing it into water or another aqueous medium (for example, a sweetened or flavoured preparation) and then used for drinking.

Alternatively, solution preconcentrates according to the invention may be filled into gelatin capsules intended for oral administration by swallowing whole. The capsules may be either soft gelatin capsules or two piece hard gelatin capsules. The capsules will most conveniently be filled using the solution preconcentrate composition in liquid form (i.e. at above its melting point). If the melting point is above ambient temperature, the contents of the capsules will solidify as they cool.

As aforesaid, if a two piece hard gelatin capsule is used, it is preferred to use a composition formulated such that it will remain a solid or a non-flowing semi-solid at temperatures as high as 40° C. to avoid the need to seal the capsules.

The invention will be more fully understood by the following examples which are illustrative but not limiting of compositions within the scope of the invention.

EXAMPLE 1

The following ingredients were placed in a test tube:

| Cyclosporine | 1.0 g |
| --- | --- |
| Propylene glycol | 1.0 g |
| Tocophersolan | 7.6 g |

EXAMPLE 2

The following ingredients were placed in a test tube:

| Cyclosporine | 1.0 g |
| --- | --- |
| Hexanol | 1.0 g |
| Tocophersolan | 7.6 g |

EXAMPLE 3

The following ingredients were placed in a test tube:

| Cyclosporine | 1.0 g |
| --- | --- |
| Benzyl alcohol | 1.0 g |
| Tocophersolan | 7.6 g |

EXAMPLE 4

The following ingredients were placed in a test tube:

| Cyclosporine | 1.0 g |
| --- | --- |
| Phenethyl alcohol | 1.0 g |
| Tocophersolan | 7.6 g |

EXAMPLE 5

The following ingredients were placed in a test tube:

| Cyclosporine | 1.0 g |
| --- | --- |
| Propylene glycol | 1.0 g |
| Tocophersolan | 5.0 g |
| Sodium dodecyl sulfate | 0.4 g |

In the case of each of examples 1 to 5, the test tube was closed tightly with a cap, and rotated in an oven at a temperature of above 40° C. The contents of each test tube gradually inter-dissolved to form a clear solution.

In each case, when drops of the resultant liquid composition were added to water, the composition gradually dissolved in the water to form a clear or virtually clear solution. Similarly, when the compositions were cooled to below their melting points, and particles of the composition were added to water, the solid or semi-solid particles also gradually dissolved to form a clear or virtually clear solution.

EXAMPLE 6

The following ingredients were placed in a test tube:

| Cyclosporine | 1.0 g |
| --- | --- |
| Propylene glycol | 1.0 g |

| | |
|---|---|
| Tocophersolan | 7.5 g |
| Carbowax 8000 | 0.2 g |

The test tube was closed tightly with a cap, and rotated in an oven at a temperature of about 65° C. The contents of the test tube gradually inter-dissolved to form a clear solution. When drops of the resultant composition were added to water, they gradually dissolved in the water to form a clear or virtually clear solution.

The composition of this example 6 is a solid or semi-solid at room temperature and remains a non-flowing semi-solid at temperatures up to about 40° C.

This composition was reheated to above its melting point, and, using a dropper, size 00 two-piece hard gelatin capsules were filled with 970 mg each of this composition; the capsules were then closed. Since the composition contained 100 mg cyclosporine per 970 mg total, each capsule thus contained 100 mg cyclosporine and was suitable for ingestion as a 100 mg dose.

The contents of the capsules solidified as the capsules cooled, and since the contents remained a non-flowing semi-solid up to at least 40° C. there was no need to seal the capsules to prevent out leakage of the contents.

INDUSTRIAL APPLICABILITY

From the foregoing description it will be apparent that the present invention provides improved compositions for the administration and absorption of cyclosporins.

The embodiments of the invention in which an exclusive property or privilege is claimed are defined as follows:

1. A pharmaceutical composition in the form of a solution preconcentrate comprising a cyclosporin dissolved in tocophersolan and a hydrophillic organic solvent.

2. A composition as in claim 1 wherein the cyclosporin is cyclosporine.

3. A composition as in claim 1 wherein the concentration of the cyclosporin in the composition exceeds 1 part per 15 parts by weight.

4. A composition as in claim 3 wherein the concentration of the cyclosporin in the composition is about 100 mg per gram or about 100 mg per mL.

5. A composition as in claim 3 wherein the concentration of the cyclosporin in the composition exceeds 100 mg per gram or 100 mg per mL.

6. A composition as in claim 1 wherein the hydrophillic organic solvent is propylene glycol.

7. A composition as in any of claim 1 wherein the hydrophillic organic solvent is a monoalcohol.

8. A composition as in claim 7 wherein the monoalcohol is selected from hexanol, benzyl alcohol and phenethyl alcohol.

9. A composition as in claim 1 which also comprises a second surfactant.

10. A composition as in claim 9 wherein the second surfactant is sodium dodecyl sulfate.

11. A composition as in claim 1 which further comprises an ingredient to raise the melting point.

12. A composition as in claim 11 wherein the further ingredient to raise the melting point is a polyethylene glycol having an average molecular weight of 1000 or higher.

13. A composition as in claim 1 when contained within a gelatin capsule.

14. A composition as in claim 13 wherein the gelatin capsule is a two-piece hard gelatin capsule.

15. A composition as in claim 14 wherein the melting point of the composition is sufficiently high that it remains a non-flowing semi-solid at temperatures as high as 40° C. and the capsule is unsealed.

* * * * *